(12) United States Patent
Tecco et al.

(10) Patent No.: US 8,173,143 B2
(45) Date of Patent: May 8, 2012

(54) PERSONAL SKIN CARE COMPOSITIONS CONTAINING ANTI-FLAMMATORY AND ANTI-MICROBIAL AGENTS

(76) Inventors: Michelle A. Tecco, Frisco, TX (US); Clifton Sanders, Plano, TX (US)

(*) Notice: Subject to any disclaimer, the term of this patent is extended or adjusted under 35 U.S.C. 154(b) by 1032 days.

(21) Appl. No.: 11/144,003

(22) Filed: Jun. 2, 2005

(65) Prior Publication Data

US 2006/0275236 A1 Dec. 7, 2006

(51) Int. Cl.
*A61K 8/02* (2006.01)
(52) U.S. Cl. ........................................ 424/401
(58) Field of Classification Search .................. None
See application file for complete search history.

(56) References Cited

U.S. PATENT DOCUMENTS

| | | | |
|---|---|---|---|
| 5,945,090 A * | 8/1999 | Randall et al. | 424/59 |
| 6,338,855 B1 | 1/2002 | Albacarys et al. | |
| 6,599,513 B2 | 7/2003 | Deckers et al. | |
| 6,800,292 B1 | 10/2004 | Murad | |
| 6,881,427 B2 * | 4/2005 | Mayne et al. | 424/757 |
| 2002/0086039 A1 * | 7/2002 | Lee et al. | 424/401 |
| 2002/0114820 A1 | 8/2002 | Deckers et al. | |
| 2002/0192245 A1 * | 12/2002 | Jensen et al. | 424/401 |
| 2004/0092414 A1 | 5/2004 | Clapp et al. | |
| 2004/0096414 A1 | 5/2004 | Mori et al. | |
| 2004/0170670 A1 | 9/2004 | Smith et al. | |
| 2005/0009017 A1 | 1/2005 | Kubota et al. | |
| 2005/0013784 A1 | 1/2005 | Trigg et al. | |
| 2005/0069514 A1 | 3/2005 | Maleedy | |
| 2005/0232894 A1 * | 10/2005 | Weiner et al. | 424/70.28 |

OTHER PUBLICATIONS

"UGL complex", product specifications, Barnet products corp., Apr. 23, 2002.*
See STIC search report (pp. 19-22, 53, and 58-59): Molaro "Sun Smarts" 2001; Dermatology Times "Moisturizer with Teamine aids collagen synthesis" Mar. 2002; or Business Wire "Men Want what women have" Apr. 13, 2005.*

* cited by examiner

*Primary Examiner* — Bethany Barham
(74) *Attorney, Agent, or Firm* — Jon Fallon, Esq.

(57) ABSTRACT

Personal care compositions suitable for use in skin care applications, which effectively deliver and/or deposit anti-inflammatory and anti-microbial agents, which are relatively non-irritating, and thus suitable for use by people having irritated or sensitive skin, particularly the skin around the eyes of a user. The personal care composition comprises a first formulation that provides anti-irritant and anti-inflammatory properties that can be easily reformulated to a second formulation that includes an anti-microbial agent by simply adding an anti-microbial agent without having to completely begin with a new formula and without compromising the properties found in the first formulation.

9 Claims, No Drawings

8,173,143 B2

PERSONAL SKIN CARE COMPOSITIONS CONTAINING ANTI-FLAMMATORY AND ANTI-MICROBIAL AGENTS

FIELD OF THE INVENTION

This invention relates to compositions suitable for use in personal care, and in particular skin care compositions, which effectively deliver anti-inflammatory and anti-microbial agents into and onto the skin that are relatively non-irritating and thus suitable for people with irritated or sensitive skin, particularly the skin around the eyes of a user.

Problem

It is a problem in the field of personal skin care compositions to have a skin-softening product that possesses concurrently both anti-irritant and anti-inflammatory properties. Yet, a need for such a product exists today. This is due to the common practice of consumers trying or experimenting with different skin care products to find the one that best suits the needs of their skin. Oftentimes, this experimentation leads to irritation and inflammation disorders of the skin, such as atopic or allergic dermatitis. Generally, once the skin is irritated by this practice, consumers must stop using skin care products until their skin becomes non-irritated or healed. It becomes a problem with consumers who wish to gain the benefits of using skin care products but that cannot use them due to the irritated or inflamed condition of their skin. In addition, other consumers have very sensitive skin and they are not able to use skin care products due to the high sensitivity of their skin to the chemical compositions of personal skin care products. These consumers are not able to enjoy many of the benefits of today's skin care products, including the benefits of softening skin cells, reducing inflammation of skin cells, and ridding skin cells of microbial activity.

Further, it is a problem for manufacturers of personal skin care products to formulate a product possessing anti-irritant and anti-inflammatory properties that can easily and conveniently be reformulated to provide additional properties, such anti-microbial properties without compromising any of the existing properties of the product. Typically, such reformulations require completely different base formulations of ingredients for each product. One reason for this is that anti-microbial ingredients are generally irritants to the skin and thus they counter the benefits of the anti-irritant and anti-inflammatory skin moisturizer. For example, on an irritation factor scale of 0 to 5 with 0 being a low irritation factor and 5 being a high irritation factor, a typical anti-irritant skin moisturizer may be 0.4 without an anti-microbial component and 1.0 with an anti-microbial component. Therefore, producing a skin moisturizer with an anti-microbial component raises the irritation factor of the overall skin moisturizer.

Yet another problem faced by manufacturers of skin care products is producing a product that is capable of providing smooth skin care with a formulation that is low in irritation to the skin. Typically, this problem arises when commonly known and used TEA acid systems are used with other ingredients having low irritation properties. When these ingredients are mixed together to form an emulsion, extra hydroxyl ions are found in these emulsions that increase the irritation rates of the emulsion.

Solution

The above described problems are solved and a technical advance achieved by the present personal skin care composition that provides the user with a skin moisturizer having a very low irritant factor with the added benefits of being an anti-inflammatory agent for the skin. Users suffering from irritated skin or those users with high sensitivity towards skin moisturizers can use the present therapeutic skin moisturizer and enjoy the benefits of its anti-inflammatory properties without further irritating their skin.

In addition, the present therapeutic skin moisturizer having anti-irritant and anti-inflammatory properties can be easily reformulated to provide additional anti-microbial properties without completely reformulating the product or starting with a completely new base formulation. The personal skin care composition having anti-irritant and anti-inflammatory properties enables a convenient reformulation to incorporate the anti-microbial ingredient without increasing the irritation factor of the product or compromising the effectiveness of its anti-irritant and anti-inflammatory properties. This enables a manufacturer to formulate a low irritant skin moisturizer that has anti-inflammatory properties, which can quickly and easily be reformulated to further include anti-microbial properties without having to completely start with a different base formulation.

The present skin care composition has an extremely low irritant factor base composition that has an amount of hydroxyl ions that are stoichiometrically balanced by the stearates added to the formulation. Once the hydroxyl ions are stoichiometrically neutralized, a very innocuous gel is added to the composition, followed by the addition of a mixture of ingredients possessing anti-inflammatory and skin-softening properties.

DETAILED DESCRIPTION OF THE PREFERRED EMBODIMENTS

All weights, measurements and concentrations herein are measured at 25 degrees centigrade on the composition in its entirety, unless otherwise specified. Unless otherwise indicated, all percentages of compositions referred to herein are weight percentages of the total composition (i.e. the sum of all components present) and all ratios are weight ratios. Unless otherwise indicated, all polymer molecular weights are weight average molecular weights. Unless otherwise indicated, the content of all literature sources referred to within this text are incorporated herein in full by reference. Except where specific examples of actual measured values are presented, numerical values referred to herein should be considered to be qualified by the word "about".

The lipophilic phase according to the present personal skin care composition may comprise any water immiscible material that is liquid at ambient conditions; any material that is solid at ambient conditions, has a melting temperature of less than 100 degrees centigrade and melts to form a water immiscible liquid; mixtures of such materials. As used herein in relation to the lipophilic phase, the term "water immiscible" includes materials having a Hildebrand Solubility Parameter of around 5-12 calories/cc (209-502 kJ/m$^2$). The solubility parameter is defined as the sum of all attractive forces radiating out of a molecule. The total Van der Waals force is called the Hildebrand Solubility Parameter and can be calculated using Hildebrand's equation using boiling point and MW data. Methods and a computer program for calculating the Hildebrand Solubility Parameter are disclosed by C. D. Vaughan in J. Cosmet. Chem. 36, 319-333 (September/October 1985).

Materials comprised within the lipophilic phase may have any polarity and may include aliphatic or aromatic hydrocarbons, esters, alcohols, ethers, carbonates, fluorocarbons, silicones, fluorosilicones or derivatives thereof. Solid materials that may be present in the lipophilic phase include waxes. As used herein, the term "wax" includes natural and synthetic waxes. The class of natural waxes includes animal waxes, such as beeswax, lanolin, shellac wax and Chinese insect wax; vegetable waxes, such as carnauba, candelilla, bayberry and sugar cane; mineral waxes, such as ceresin and ozokerite; petrochemical waxes, such as microcrystalline wax and petrolatum. The class of synthetic waxes includes ethylenic polymers and polyol ether-esters, chlorinated naphthalenes and Fischer-Tropsch waxes. For more details, please refer to see Rompp Chemie Lexikon, Georg Thieme Verlag, Stuttgart, 9.sup.th Edition, 1995 under "Wachse".

Advantageously, materials comprised within the lipophilic phase, including the melted waxes, have a viscosity in the range from 0.005 to 30,000 $cm^2/s$ (0.5 to 3,000,000 cst), preferably from 0.005 to 20,000 $cm^2/s$ (0.5 to 2,000,000 cst), more preferably from 0.005 to 3500 $cm^2/s$ (0.5 to 350,000 cst). The lipophilic phase may comprise from a few percent up to over 50% wt of the personal care composition. Advantageously, the lipophilic phase comprises less than 90% wt of the personal care composition. The hydrophilic phase of the emulsions according to the invention comprises water and may also comprise additional water-soluble components, such as alcohols; humectants, including polyhydric alcohols (e.g. glycerine and propylene glycol); active agents such as d-panthenol, vitamin $B_3$ and its derivatives (such as niacinamide) and botanical extracts; thickeners and preservatives. The water-soluble emulsification polymers according to the invention have a molecular weight of at least 3000 Daltons, since below this level, the resulting emulsions have less than a desirable feel to the skin. Skin feel improves with increasing molecular weight and it is preferred that the water-soluble emulsification polymers according to the invention have a molecular weight above 7500 Daltons, more preferably above 9000 Daltons and, more preferably still, above 10,000 Daltons.

In one embodiment, the present therapeutic skin moisturizer includes a base formula that includes a very low irritation factor and an anti-inflammatory component. This embodiment includes a lipophilic phase that is prepared and combined with a hydrophilic phase. Then an anti-inflammatory phase is added to the mixture followed by an addition of another ingredient possessing additional anti-inflammatory properties to produce a personal skin care composition having anti-irritant and anti-inflammatory properties.

In another embodiment, of the present skin moisturizer further includes an anti-microbial component. This embodiment includes a lipophilic phase that is prepared and combined with a hydrophilic phase. Then an anti-inflammatory phase is added to the mixture followed by an addition of another ingredient possessing additional anti-inflammatory properties. Then a final phase containing an anti-microbial property is added to the mixture to produce a personal skin care composition having anti-irritant, anti-inflammatory, and anti-microbial properties.

Hydrophilic Phase

The hydrophilic phase of the present personal skin care composition includes water in an amount to provide a desired consistency for the product. In one embodiment, the personal skin care composition contains water in the amount preferably between 50% to 70% by weight. Additionally, this amount of water can be increased or decreased as desired.

The hydrophilic phase of the present personal skin care composition further includes water soluble preservatives. One exemplary preservative of the hydrophilic phase includes Phenonip™, which is a tradename for a mixture of paraben compounds made by Clariant and it contains the following components: phenoxyethanol (CAS # 122-99-6), ethylparaben (CAS #99-76-3), butylparaben (CAS #94-26-8), ethylparaben (CAS #120-47-8), and propylparaben (CAS #94-13-3). In addition to being a preservative, it is further provides microbial contamination of the personal skin care composition and is effective against Gram-positive and Gram-negative bacteria, yeasts, and molds. In one embodiment, the personal skin care composition contains Phenonip™ in an amount preferably between 0.10% to 0.80% by weight. Additionally, this amount of preservative can be increased or decreased as desired.

The hydrophilic phase of the present personal skin care composition may further include additional preservatives. An additional exemplary preservative is sodium dehydroacetate. In one embodiment, the personal skin care composition contains the preservative sodium dehydroacetate in an amount preferably between 0.10% to 0.30% by weight. In this embodiment, the personal skin care composition further contains the preservative isopentyldiol in an amount preferably between 1.0% to 5.0% by weight.

Other known preservative agents that can be used and include, but are not limited to, hydroquinone, pyrocatechol, resorcinol, 4-n-hexyl resorcinol, captan (i.e., 3a,4,7,7a-tetrahydro-2-((trichloromethyl)thio)-1H-isoindole-1,3(2H)-dione), benzethonium chloride, benzoic acid, benzyl alcohol, cetylpyridinium chloride, chlorobutanol, dehydroacetic acid, o-phenylphenol, phenol, phenylethyl alcohol, potassium benzoate, potassium sorbate, sodium benzoate, sodium propionate, sorbic acid, thimerosal, thymol, chlorothymol, alcohols, chlorobutanol, phenoxy-2-ethanol, benzyl alcohol, .beta.-phenylethyl alcohol, chlorhexidine, 6-acetoxy-2,4-dimethyl-m-dioxane 2,4,4'trichloro-2'-hydroxy-diphenylether, imidizoldinylether urea compound, bromo-2-nitropropanediol-1,3,5-bromo-5-nitrol-1,3 dioxane 2-methyl 14-isothiazolin-3-one and 5 chloro derivative 1-(3-chloroallyl)-3,5,7-triazo 1-azoniaadamantane chloride (Dowicil 200), phenylmercuric compounds such as phenylmercuric borate, phenylmercuric nitrate and phenylmercuric acetate, formaldehyde, formaldehyde generators such as the preservatives Germall II™ and Germall 115™ (imidazolidinyl urea, available from Sutton Laboratories, Charthan, N.J.), Germaben, Germaben I, Germaben II, morpholines, salicylic and benzoic acids, sodium and potassium iodides, flucytosine, 5-flucytosine, griseofulvin, terbinafine, cidofovir, famicoclovir, valacyclovir, echinocandins, pneumocandins, pradimicins, benanomicins, nikkomycins, amorolfine, polyoxins, duanorubicin citrate, doxorubicin hydrchlolide, tolnaftate, ciclopirox, butenafine, and ergestrol biosynthesis inhibitors.

Other preservative and emollients include hydroxypivalyl hydroxypivalate and its alkoxylated derivatives, TMPD, TMPD alkoxylates, ethanol, isopropanol, butanol, 1,2-cyclohexanedimethanol, 1,4-cyclohexanedimethanol, HPHP glycol, 1,2-hexanediol, ethylene glycol butyl ether, hexylene glycol, isoprene glycol, sorbitan ethoxylates, 2-butoxyethanol, $C_6$-$C_{12}$ diols/triols and ester diols/triols and their alkoxylated derivatives, glycol ethers, and mixtures thereof.

The hydrophilic phase of the present personal skin care composition may further include thickening agents. Generally, these thickening agents also provide an emulsion stabilizing function to the personal skin care composition. An exemplary thickening agent is carbomer and water. In one embodiment, the personal skin care composition contains carbomers available from B.F. Goodrich under the tradename, "Carbopol ETD 2020" and water in an amount preferably between 10% to 20% by weight. In one embodiment, the personal skin care composition contains an additional thickener, tridecyl stearate, in an amount preferably between 2.5% to 7.5%.

Additional exemplary hydrophilic thickening agents nonexclusively include acrylate copolymers, hydroxyethylcellulose modified with cetyl ether groups available from Hercules under the tradename, "Natrosol Plus", polyvinylmethyl ether/maleic an hydride (PVM/MA) decadiene crosspolymer available from International Specialty Products under the tradename, "Stabileze QM," and copolymers and mixtures thereof, with carbomers being preferred. Examples of suitable acrylate copolymers nonexclusively include acrylate copolymers available from Rohm & Haas under the tradename, "Aculyn 33," acrylates/aminoacrylates copolymer available from National Starch & Chemical Company under the tradename, "Structure Plus," acrylates/steareth-20 itaconate copolymer available from National Starch & Chemical Company under the tradename, "Structure 2001," acrylates/ceteth-20 itaconate copolymer available from National Starch & Chemical Company under the tradename, "Structure 3001," acrylates/steareth-20 methacrylate copolymer available from Rohm & Haas under the tradename, "Aculyn 22," and copolymers and mixtures thereof.

Hydrophilic gelling agents include carboxyvinyl polymers, acrylic copolymers such as acrylate/alkylacrylate copolymers, polyacrylamides, polysaccharides, such as hydroxypropylcellulose, natural gums and clays, and, as lipophilic gelling agents, representative are the modified clays such as bentones, fatty acid metal salts such as aluminum stearates and hydrophobic silica, or ethylcellulose and polyethylene.

The present skin care composition includes additional thickening agents such as alkyl silicones, alkyl trimethylsilanes, beeswax, behenyl behenate, behenyl benzoate, $C_{24}$-$C_{28}$ alkyl dimethicone, $C_{30}$ alkyl dimethicone, cetyl methicone, stearyl methicone, cetyl dimethicone, stearyl dimethicone, cerotyl dimethicone, candelilla wax, carnauba, synthetic carnauba, PEG-12 carnauba, cerasin, hydrogenated microcrystalline wax, jojoba wax, microcrystalline wax, lanolin wax, ozokerite, paraffin, synthetic paraffin, cetyl esters, behenyl behenate, $C_{20}$-$C_{40}$ alkyl behenate, $C_{12}$-$C_{15}$ lactate, cetyl palmitate, stearyl palmitate, isosteryl behenate, lauryl behenate, stearyl benzoate, behenyl isostearate, cetyl myristate, cetyl octanoate, cetyl oleate, cetyl ricinoleate, cetyl stearate, decyl oleate, di-$C_{12}$-$C_{15}$ alkyl fumerate, dibehenyl fumerate, myristyl lactate, myristyl lignocerate, myristyl myristate, myristyl stearate, lauryl stearate, octyidodecyl stearate, octyldodecyl stearoyl stearate, oleyl arachidate, oleyl stearate, tridecyl behenate, tridecyl stearoyl stearate, pentaerythrityl tetrabehenate, pentaerythrityl hydrogenated rosinate, pentaerythrityl distearate, pentaerythrityl tetraabeite, pentaerythrityl tetracocoate, pentaerythrityl tetraperlargonate, pentaerythrityl tetrastearate, ethylene vinyl acetate, polyethylene, hydrogenated cottonseed oil, hydrogenated vegetable oil, hydrogenated squalene, hydrogenated coconut oil, hydrogenated jojoba oil, hydrogenated palm oil, hydrogenated palm kernel oil, hydrogenated olive oil, polyamides, metal stearates and other metal soaps, $C_{30}$-$C_{60}$ fatty alcohols, $C_{20}$+ fatty amides, polypropylene, polystyrene, polybutane, polybutylene terephthalate, polydipentane, polypropylene, zinc stearate, dodecyl laurate, stearyl palmitate, octadecyl hexadecanoate, octadecyl palmitate, stearyl behenate, docosyl octanoate, tetradecyl-octadecanyl behenate, hexadecyl-cosanyl hexacosanate, shellac wax, glycol montanate, fluoranated waxes, $C_{20}$-$C_{40}$ alkyl hydroxystearyl stearate and mixtures of such compounds. Examples of suitable branched esters include tetradecyl-octadecanyl behenate and hexadecyl-cosanyl-hexacosanate.

Lipophilic Phase

The lipophilic phase of the present personal skin care composition includes emulsifiers, penetrating agents that are phospholipids. In one embodiment, the personal skin care composition contains hydrogenated lecithin in an amount preferably between 1.0% to 5.0% by weight. Additionally, this amount of preservative can be increased or decreased as desired. Other exemplary emulsifiers include phosphatidyl choline, phosphatidyl serine, phosphatidyl ethanolamine, phosphatidyl inositol, phosphatidyl glycerol, sphingomyelin, soybean lecithin, corn lecithin, cotton seed oil lecithin, egg yolk lecithin, egg white lecithin, etc.; hydrogenated lecithins; and phospholipid derivatives as formed by introducing polyethylene glycol or aminoglycans into those phospholipids. One or more of those phospholipids may be in the composition. Of those phospholipids, preferred are soybean lecithin, egg yolk lecithin, hydrogenated soybean lecithin, and hydrogenated egg yolk lecithin.

The present personal skin care composition includes additional emollients and emulsifiers, such as long-chain saturated fatty alcohols, such as behenyl alcohol. In one embodiment, the personal skin care composition contains behenyl alcohol in an amount preferably between 0.5% to 3.0% by weight. Other additional exemplary emollients and emulsifiers include of $C_{14}$-$C_{22}$ fatty alcohols, $C_{12}$-$C_{22}$ fatty acids, and $C_{12}$-$C_{22}$ fatty alcohol ethoxylates having an average degree of ethoxylation ranging from 2 to about 30, and mixtures thereof. Preferred immobilizing agents include $C_{16}$-$C_{18}$ fatty alcohols, most preferably crystalline high melting materials selected from the group consisting of cetyl alcohol, stearyl alcohol, and mixtures thereof. In one embodiment, the personal skin care composition contains cetyl alcohol in an amount preferably between 0.5% and 8.5% by weight.

The present personal skin care composition includes a licorice extract ester derivatives including saturated and unsaturated esters of glycerrhetic acid and glycyrrhizic acid in which the ester portion of the molecule contains from 2 to 24 carbon atoms, more preferably from 10 to 24 carbon atoms, still more preferably from 16 to 24 carbon atoms. In one embodiment, the personal skin care composition contains stearyl glycyrrhetinate, sold under the tradename NET-STG by Barnet Products Corporation (Englewood Cliffs, N.J.), in an amount preferably between 0.1% to 3.8% by weight.

Other additional exemplary licorice extract ester derivatives for use in accordance with the present invention include but are not limited to monoammonium glycyrrhizinate, monopotassium glycyrrhizinate, dipotassium glycyrrhizinate, 1-beta-glycyrrhetic acid, 3-stearyloxy-glycyrrhetinic acid, disodium 3-succinyloxy-beta-glycyrrhetinate, and the like.

In one embodiment, the present personal skin care composition includes an oil soluble form of Vitamin C, such as tetrahexyldecyl ascorbate in an amount preferably between 0.1% to 2.5% by weight.

The lipophilic phase of the present personal skin care composition also includes at least one oil, such as octyldecyl myristate in an amount preferably between 2.5% to 8.0% by weight. Other exemplary oils include hydrocarbon-based oils such as liquid paraffin or liquid petroleum jelly, mink oil, turtle oil, soybean oil, perhydrosqualene, sweet almond oil, beauty-leaf oil, palm oil, grapeseed oil, sesame seed oil, corn oil, parleam oil, arara oil, rapeseed oil, sunflower oil, cottonseed oil, apricot oil, castor oil, avocado oil, jojoba oil, olive oil or cereal germ oil; esters of lanolic acid, of oleic acid, of lauric acid or of stearic acid; fatty esters, such as isopropyl myristate, isopropyl palmitate, butyl stearate, hexyl laurate, diisopropyl adipate, isononyl isononate, 2-ethylhexyl palmitate, 2-hexyldecyl laurate, 2-octyldecyl palmitate, 2-octyldodecyl myristate or lactate, 2-diethylhexyl succinate, diisostearyl malate, glyceryl triisostearate or diglyceryl triisostearate; higher fatty acids such as myristic acid, palmitic acid, stearic acid, behenic acid, oleic acid, linoleic acid, linolenic acid or isostearic acid; higher fatty alcohols such as cetanol, stearyl alcohol or oleyl alcohol, linoleyl alcohol or linolenyl alcohol, isostearyl alcohol or octyldodecanol; silicone oils such as polydimethylsiloxanes (PDMS), which are optionally phenylated such as phenyltrimethicones, or optionally substituted with aliphatic and/or aromatic groups that are optionally fluorinated, or with functional groups such as hydroxyl, thiol and/or amine groups; polysiloxanes modified with fatty acids, with fatty alcohols or with polyoxyalkylenes, fluorosilicones and perfluoro oils.

The lipophilic phase of the present personal skin care composition preferably also includes emollients, such as squalane in an amount between 0.1% to 10.0% by weight. Other exemplary emollients include castor oil, polybutene, sweet almond oil, avocado oil, calophyllum oil, ricin oil, vitamin E acetate, olive oil, silicone oils such as dimethylopolysiloxane and cyclomethicone, linolenic alcohol, oleyl alcohol, the oil of cereal germs such as the oil of wheat germ, isopropyl palmitate, octyl palmitate, isopropyl myristate, hexadecyl stearate, butyl stearate, decyl oleate, acetyl glycerides, the octanoates and benzoates of ($C_{12}$-$C_{15}$) alcohols, the octanoates and decanoates of alcohols and polyalcohols such as those of glycol and glyceryl, ricinoleates esters such as isopropyl adipate, hexyl laurate and octyl dodecanoate, dicaprylyl maleate, hydrogenated vegetable oil, phenyltrimethicone, jojoba oil and aloe vera extract.

The lipophilic phase of the present personal skin care composition preferably also includes viscosity builders, such as cetearyl alcohol and polysorbate 60 in an amount between 0.5% and 5.5% by weight. Other exemplary viscosity builders include ceteareth-25 and ceteareth-6, i.e., polyethylene glycol ethers of cetearyl alcohol with 25 and 6 ethylene glycol units respectively.

The present personal skin care composition includes skin penetrating agents such as tribehenin in an amount between 0.1% and 2.0% by weight. Other exemplary penetrating agents include waxes which are solid or semi-solid at room temperature, such as animal waxes, plant waxes, mineral waxes, silicone waxes, synthetic waxes, and petroleum waxes. More specifically, these waxes include bayberry, beeswax, candelilla, carnauba, ceresin, cetyl esters, hydrogenated jojoba oil, hydrogenated jojoba wax, hydrogenated microcrystalline wax, hydrogenated rice bran wax, japan wax, jojoba butter, jojoba esters, jojoba wax, lanolin wax, microcrystalline wax, mink wax, montan acid wax, montan wax, ouricury wax, ozokerite, paraffin, cetyl alcohol, beeswax, PEG-20 sorbitan beeswax, PEG-8 beeswax, rice bran wax, shellac wax, spent grain wax, sulfurized jojoba oil, synthetic beeswax, synthetic candelilla wax, synthetic carnauba wax, synthetic japan wax, synthetic jojoba oil, synthetic wax, polyethylene, stearoxy dimethicone, dimethicone behenate, stearyl dimethicone, and the like, as well synthetic homo- and copolymer waxes such as PVP/eicosene copolymer, PVP/hexadecene copolymer, and the like.

The present personal skin care composition includes neutralizing agents may be included to neutralize the carboxylic acid/carboxylate copolymers herein. Nonlimiting examples of such neutralizing agents include sodium hydroxide, potassium hydroxide, ammonium hydroxide, monethanolamine, diethanolamine, triethanolamine, diisopropanolamine, aminomethylpropanol, tromethamine, tetrahydroxypropyl ethylenediamine, and mixtures thereof. In one embodiment, the present personal skin care composition includes sodium hydroxide and water in an amount between 0.1% to 3.0% by weight.

The present personal skin care composition preferably includes high viscosity silicone compounds herein include those having a molecular weight of from about 200,000 to about 540,000 selected from those mentioned above, preferably selected from the group consisting of dimethiconol, fluorosilicone dimethicone, and mixtures thereof, more preferably essentially dimethiconol. Particularly preferred dimethiconols are those having dimethylpolysiloxane repeating units, and terminated with hydroxy groups, wherein the dimethylsiloxane portion is made of from about 2700 to about 4500 repeating units. In one embodiment, the personal skin care composition includes dimethicone in an amount between 1.0% and 4.0% by weight.

In addition to the thickeners described above, gums may be used to provide a thickening agent to the personal skin care composition. In one embodiment, the personal skin care composition includes biosaccharide gum-1 (e.g. FUCOGEL 1000™ available from Solabia (France)) in an amount between 0.5% and 7.5%. Other exemplary gums include xanthan, karaya, gellan, wellan, arabic, carrageanan, and locust bean. Also suitable are alginate and agarose.

The present personal skin care composition includes examples of active ingredients that can be used in the composition of the invention that can be cited are extracts from algae, fungi, plants, yeasts, bacteria; steroids; antibacterial active ingredients such as 2,4,4'-trichloro-2'-hydroxy diphenyl ether (or triclosan), 3,4,4'-trichlorocarbanilide (or triclocarban) and the acids indicated above, especially salicylic acid and its derivatives; tightening agents; ceramides; essential oils; and mixtures thereof; and any active ingredient that is appropriate to the end use of the composition.

In one aspect of the present personal skin care composition, a UGL complex can be used to provide the necessary amounts of glucosamine HCl, algae extract, yeast extract, and urea. One exemplary manufacturer of an UGL complex is Barnet Products Corporation. In one embodiment, a UGL complex containing glucosamine HCl, algae extract, yeast extract, and urea is included in an amount between 1.0% and 10.0% by weight.

In one embodiment of the present personal skin care composition, an anti-microbial agent is included in the formulation to provide anti-irritant, anti-inflammatory product having anti-microbial properties. Some exemplary anti-microbial compounds include benzalkonium chloride, tricolsan, proflactin, beta-lactam drugs, quinolone drugs, ciprofloxacin, norfloxacin, tetracycline, erythromycin, amikacin, 2,4,4'-trichloro-2'-hydroxy diphenyl ether, 3,4,4'-trichlorobanilide, phenoxyethanol, phenoxy propanol, phenoxyisopropanol, doxycycline, capreomycin, chlorhexidine, chlortetracycline, oxytetracycline, clindamycin, ethambutol, hexamidine isethionate, metronidazole, pentamidine, gentamicin, kanamycin, lineomycin, methacycline, methenamine, minocycline, neomycin, netilmicin, paromomycin, streptomycin, tobramycin, miconazole, tetracycline hydrochloride, erythromycin, zinc erythromycin, erythromycin estolate, erythromycin stearate, amikacin sulfate, doxycycline hydrochloride, capreomycin sulfate, chlorhexidine gluconate, chlorhexidine hydrochloride, chlortetracycline hydrochloride, oxytetracycline hydrochloride, clindamycin hydrochloride, ethambutol hydrochloride, metronidazole hydrochloride, pentamidine hydrochloride, gentamicin sulfate, kanamycin sulfate, lineomycin hydrochloride, nnethacycline hydrochloride, methenamine hippurate, methenamine mandelate, minocycline hydrochloride, neomycin sulfate, netilmicin sulfate, paromomycin sulfate, streptomycin sulfate, tobramycin sulfate, miconazole hydrochloride, amanfadine hydrochloride, amanfadine sulfate, octopirox, parachlorometa xylenol, nystatin, tolnaftate, clotrimazole, cetylpyridinium chloride (CPC), piroctone olamine, selenium sulfide, ketoconazole, triclocarbon, triclosan, triclocarban (also known as trichlorocarbanilide), hexachlorophene, (3,4,5-tribromosalicylanilide), zinc pyrithione, itraconazole, asiatic acid, hinokitiol, mipirocin and those described in EP 680,745, clinacycin hydrochloride, benzoyl peroxide, benzyl peroxide, minocyclin, phenoxy isopropanol, and mixtures thereof. In one embodiment, the personal skin care composition includes benzalkonium chloride in an amount between 0.05% and 0.35% by weight.

The following examples further describe and demonstrate embodiments within the scope of the present invention. The examples are given solely for the purpose of illustration and are not to be construed as limitations of the present invention, as many variations thereof are possible without departing from the spirit and scope of the invention. Ingredients are identified by chemical or CTFA name, or otherwise defined below. All amounts are percentages by weight based on the total composition weight.

TABLE 1

Anti-Irritant/Anti-Inflammatory Formulation Compositions

| Phase | Ingredient | Ranges |
|---|---|---|
| 01 | Water | 50-70% |
| 01 | Phenonip | 0.10-0.80% |
| 01 | Carbomer and Water | 10-20% |
| 01 | Sodium Dehydroacetate | 0.10-0.30% |
| 01 | Isopentyldiol | 1.0-5.0% |
| 01 | Tridecyl Stearate | 2.5-7.5% |
| 02 | Hydrogenated Lecithin | 1.0-5.0% |
| 02 | Behenyl Alcohol | 0.5-3.0% |
| 02 | Stearyl Glycyrrhetinate | 0.1-3.8% |
| 02 | Tetrahexyldecyl Ascorbate | 0.1-2.5% |
| 02 | Octododecyl Myristate | 2.5-8.0% |
| 02 | Cetyl Alcohol | 0.5-8.5% |
| 02 | Squalane | 0.1-10% |
| 02 | Cetearyl Alcohol and Polysorbate 60 | 0.5-5.5% |
| 02 | Tribehenin | 0.1-2.0% |
| 03 | Sodium Hydroxide and Water | 0.1-3.0% |
| 03 | Dimethicone | 1.0-4.0% |
| 03 | Glucosamine HCl | 0.1-10.0% |
| 03 | Algae Extract | 0.1-10.0% |
| 03 | Yeast | 1.0-10.0% |
| 03 | Urea | 0.1-10.0% |
| 04 | Biosaccharide Gum-1 | 0.5-7.5% |

EXAMPLE 1

Anti-Irritant/Anti-Inflammatory Formulation

The preparation of the hydrophilic phase (01) is as follows. The following ingredients are put into a first reaction vessel: water, Phenonip™, sodium dehydroacetate, isopentyldiol, and tridecyl stearate. These ingredients are heated to a temperature of approximately 80 degrees centigrade and mixed.

The preparation of the lipophilic phase (02) is as follows. The following ingredients are put into a second reaction vessel: hydrogenated lecithin, behenyl alcohol, stearyl glycyrrhetinate, tetrahexyldecyl ascorbate, octyidodecyl myristate, cetyl alcohol, squalane, and cetearyl alcohol and Polysorbate 60. These ingredients are heated to a temperature of approximately 80 degrees centigrade and mixed.

The preparation of final composition is as follows. The second reaction vessel is emptied into the first reaction vessel and then the first reaction vessel is heated to approximately 80 degrees centigrade. Then the mixture is mixed using a mixing apparatus, such as a sheer mixer, to an emulsion. Then the mixture is cooled down to about 70 degrees centigrade and the following ingredients, phase (3), are added to the mixture: sodium hydroxide and water, dimethicone, glucosamine HCl, algae extract, yeast extract, and urea. The mixture is then allowed to cool to approximately 30 degrees centigrade. Then biosaccharide gum-1, phase (4), is added into to the mixture and mixed to an emulsion.

TABLE 2

Anti-Irritant/Anti-Inflammatory/Anti-Microbial Formulation Compositions

| Phase | Ingredient | Ranges |
|---|---|---|
| 01 | Water | 50-70% |
| 01 | Phenonip | 0.10-0.80% |
| 01 | Carbomer and Water | 10-20% |
| 01 | Sodium Dehydroacetate | 0.10-0.30% |
| 01 | Isopentyldiol | 1.0-5.0% |
| 01 | Tridecyl Stearate | 2.5-7.5% |
| 02 | Hydrogenated Lecithin | 1.0-5.0% |
| 02 | Behenyl Alcohol | 0.5-3.0% |
| 02 | Stearyl Glycyrrhetinate | 0.1-3.8% |
| 02 | Tetrahexyldecyl Ascorbate | 0.1-2.5% |
| 02 | Octododecyl Myristate | 2.5-8.0% |
| 02 | Cetyl Alcohol | 0.5-8.5% |
| 02 | Squalane | 0.1-10% |
| 02 | Cetearyl Alcohol and Polysorbate 60 | 0.5-5.5% |
| 02 | Tribehenin | 0.1-2.0% |
| 03 | Sodium Hydroxide and Water | 0.1-3.0% |
| 03 | Dimethicone | 1.0-4.0% |
| 03 | Glucosamine HCl | 0.1-10.0% |
| 03 | Algae Extract | 0.1-10.0% |
| 03 | Yeast | 1.0-10.0% |
| 03 | Urea | 0.1-10.0% |
| 04 | Biosaccharide Gum-1 | 0.5-7.5% |
| 05 | Benzalkonium Chloride | 0.05-0.35% |

EXAMPLE 2

Anti-Irritant/Anti-Inflammatory/Anti-Microbial Formulation

The preparation of the hydrophilic phase (01) is as follows. The following ingredients are put into a first reaction vessel: water, Phenonip™, sodium dehydroacetate, isopentyldiol, and tridecyl stearate. These ingredients are heated to a temperature of approximately 80 degrees centigrade and mixed.

The preparation of the lipophilic phase (02) is as follows. The following ingredients are put into a second reaction vessel: hydrogenated lecithin, behenyl alcohol, stearyl glycyrrhetinate, tetrahexyldecyl ascorbate, octyldodecyl myristate, cetyl alcohol, squalane, and cetearyl alcohol and Polysorbate 60. These ingredients are heated to a temperature of approximately 80 degrees centigrade and mixed.

The preparation of final composition is as follows. The second reaction vessel is emptied into the first reaction vessel and then the first reaction vessel is heated to approximately 80 degrees centigrade. Then the mixture is mixed using a mixing apparatus, such as a sheer mixer, to an emulsion. Then the mixture is cooled down to about 70 degrees centigrade and the following ingredients, phase (3), are added to the mixture: sodium hydroxide and water, dimethicone, glucosamine HCl, algae extract, yeast extract, and urea. The mixture is then allowed to cool to approximately 30 degrees centigrade. Then biosaccharide gum-1, phase (4), is added into to the mixture and mixed to an emulsion.

In another embodiment of the present personal skin care composition, the preparation of the composition of Example 2 is as follows. The phases (1) through (4) are prepared the same as for Example 1 with the addition of the at least one anti-microbial ingredient, phase (5) being added to the mixture above. In this embodiment, benzalkonium chloride is added to the mixture above after the mixture has reached a temperature of approximately 25 degrees centigrade.

TABLE 3

Anti-Irritant/Anti-Inflammatory/Anti-Microbial Formulation Compositions

| Phase | Ingredient | |
|---|---|---|
| 01 | Water | 64.10% |
| 01 | Liposerve PP ® | 0.75% |
| 01 | Carbopol 980 ® (2%) | 10.00% |
| 01 | Sodium Dehydroacetate | 0.10% |
| 01 | Isoprene Glycol | 3.00% |
| 02 | Liponate TDS ® | 5.25% |
| 02 | Lecinol S-10 ® | 2.00% |
| 02 | Behenyl Alcohol 80 | 1.50% |
| 02 | BV-OSC ® | 0.20% |
| 02 | NET-STG | 0.10% |
| 02 | ODM-100 | 3.50% |
| 02 | Lipocol ® C | 0.75% |
| 02 | Phytlane LS | 1.00% |
| 02 | Lipowax ® P | 1.50% |
| 02 | Lipovol ® GTB | 0.75% |
| 03 | Sodium Hydroxide (18%) | 0.20% |
| 04 | Silicone HL-88 | 1.00% |
| 05 | UGL Complex | 3.00% |
| 06 | Fucogel ®1000BPC | 1.00% |
| 07 | Stepanquat ™ 50NF | 0.30% |

EXAMPLE 3

Anti-Irritant/Anti-Inflammatory/Anti-Microbial Formulation

The preparation of the hydrophilic phase (01) is as follows. The following ingredients are put into a first reaction vessel: water, Liposerve® PP, Carbopol® 980 (2%), sodium dehydroacetate, and isoprene glycol. These ingredients are heated to a temperature between approximately 70-80 degrees centigrade using a propeller mixer at moderate speed.

The preparation of the lipophilic phase (02) is as follows. The following ingredients are put into a second reaction vessel: Liponate TDS®, Lecinol S-10®, Behenyl Alcohol 80, BV-OSC®, NET-STG, ODM-100, Lipocol® C, Phytlane LS, Lipowax® P, and Lipovol® GTB. These ingredients are heated to a temperature of approximately 80 degrees centigrade and mixed until uniform.

The preparation of final composition is as follows. The second reaction vessel is emptied into the first reaction vessel and then the first reaction vessel is heated to approximately 80 degrees centigrade. Then the mixture is mixed at medium speed using a mixing apparatus, such as a sheer mixer or a propeller mixer, to an emulsion. Then the mixture is cooled down to about 70 degrees centigrade and the following ingredient, phase (3), is added to the mixture: Sodium Hydroxide (18%). The mixture is then mixed. The mixture is then allowed to cool to approximately 35 degrees centigrade. Then the Silicone HL-88 is added and mixed into the batch, which is then followed by the addition and mixing of the UGL Complex into the batch. Then the Fucogel® 1000 BPC is added and mixed into the batch, followed by the addition and mixing of the Stepanquat™ 50 NF to the batch. Finally, the pH of the batch is adjusted by further addition of amounts of UGL Complex until the desire pH of the batch is achieved. The batch is mixed to an emulsion. Preferably, the pH is adjusted to between a pH of 6.0-7.0. Additionally, the emulsion has a viscosity of LV T-E @ 0.3 rpm of 150,000 cps.

Although there has been described what is at present considered to be the preferred embodiments of the present personal skin care composition, it will be understood that the present personal skin care composition can be embodied in other specific forms without departing from the spirit or essential characteristics thereof. The present embodiments are, therefore, to be considered in all aspects as illustrative and not restrictive. The scope of the invention is indicated by the appended claims rather than the foregoing description.

SUMMARY

A personal skin care composition including from about 50% to about 70%, based on the total weight of the composition, of water; from about 0.10% to about 0.80%, based on the total weight of the composition, of a preservative; from about 10% to about 20%, based on the total weight of the composition, of a thickening agent; from about 0.1% to about 3.8%, based on the total weight of the composition, of stearyl glycyrrhetinate; from about 0.5% to about 8.5%, based on the total weight of the composition, of an emulsion agent; from about 0.1% to about 10%, based on the total weight of the composition, of squalane; from about 0.1% to about 3.0%, based on the total weight of the composition, of sodium hydroxide; and from about 1.0% to about 10%, based on the total weight of the composition, of a mixture consisting of glucosamine HCl, red algae extract, yeast extract, and urea.

Preferably, the personal skin care composition includes an anti-microbial agent. Preferably, the anti-microbial agent is at least one anti-microbial agent selected from the group consisting of benzalkonium chloride and tricolsan. Preferably, the anti-microbial agent is present in an amount from about 0.05% to about 0.35% based on the total weight of the composition. Preferably, the preservative is at least one preservative selected from the group consisting of Phenonip ™, isopentyldiol, Germaben™, Germaben I™, Germaben II™, Germal 115™, and sodium dehydroacetate. Preferably, the thickening agent is at least one thickening agent selected from the group consisting of carbomer, biosaccharide gum-1, and Carbopol™. Preferably, the emulsion agent is selected from the group consisting of cetyl alcohol, tridecyl stearate, behenyl alcohol, tetrahexyldecyl ascorbate, octododecyl myristate, hydrogenated lecithin, cetearyl alcohol, and polysorbate 60. Preferably, the personal skin care composition further includes a skin protectant selected from the group consisting of dimethicone. Preferably, the personal skin care composition further includes tribehenin.

| GLOSSARY | |
|---|---|
| DCQ2-1401 | Dimethicone/Dimethiconol available from Dow Corning. |
| Carbopol ® 981 | Trademark product (Carbomer) available from B. F. Goodrich. |
| Phenonip | Mixture of parabens tradename product available from Clariant UK Ltd. |
| Liposerve ® PP | Trademark product (Phenoxyethanol, Methylparaben, Propylparaben, and Isobutylparaben) available from Lipo Chemicals Inc. |
| Liponate ® TDS | Trademark product (Tridecyl Stearate) available from Lipo Chemicals Inc. |
| Lecinol ® S-10 | Trademark product (Hydrogenated Lecithin) available from Nikko Chemicals |
| BV-OSC ® | Trademark product (Tetrahexyldecyl Ascorbate) available from Barnet Products Corp. |
| NET-STG | Stearyl Glycyrrhetinate |
| ODM-100 | Octododecyl Myristate |
| Lipocol ® C | Trademark product (Cetyl Alcohol) available from Lipo Chemicals Inc. |
| Phytlane LS | Squalane |
| Lipowax ® P | Trademark product (Cetearyl Alcohol and Polysorbate 60) available from Lipo Chemicals Inc. |
| Lipovol ® GTB | Trademark product (Tribehenin) available from Lipo Chemicals Inc. |
| Silicone HL-88 | Trademark product (Dimethicone) available from Barnet Products Corp. |
| UGL Complex | Trademark product (Glucosamine HCl, Algae Extract, Yeast Extract, and Urea) available from Barnet Products Corp. |
| Fucogel ® 1000BPC | Trademark product (Biosaccharide Gum-1) |
| Stepanquat ™ 50NF | Trademark product (Benzalkonium Chloride) available from Stepan Products |

What is claimed:

1. A personal skin care composition consisting essentially of: (a) from about 50% to about 77%, based on the total weight of the composition, of water; (b) from about 0.6% to about 0.9%, based on the total weight of the composition, of a preservative mixture, said preservative mixture selected from the group consisting of phenoxyethanol, methylparaben, propylparaben, butylparaben, and isobutylparaben; (c) from about 8% to about 12%, based on the total weight of the composition, of a carbomer; (d) from about 4.2% to about 6.3%, based on the total weight of the composition, of tridecyl stearate; (e) from about 1.6% to about 2.4%, based on the total weight of the composition, of hydrogenated lecithin; (f) from about 1.2% to about 1.8%, based on the total weight of the composition, of behenyl alcohol; (g) from about 0.08% to about 0.12%, based on the total weight of the composition, of stearyl glycyrrhetinate; (h) from about 2.8% to about 4.2%, based on the total weight of the composition, of octyldodecyl myristate; (i) from about 0.1% to about 10%, based on the total weight of the composition, of squalane; (j) from about 0.16% to about 0.24%, based on the total weight of the composition, of an approximately 18% solution of sodium hydroxide and water; (k) from about 2.4% to about 3.6%, based on the total weight of the composition, of a mixture consisting of glucosamine HCl, red algae extract, yeast extract, and urea; (l) from about 0.24% to about 0.36%, based on the total weight of the composition, of benzalkonium chloride; (m) from about 0.16% to about 0.24%, based on the total weight of the composition, of tetrahexyldecyl ascorbate; and (n) stoichiometrically balanced amounts of hydroxyl ions and stearates, wherein the hydroxyl ions are neutralized by the stearates; and wherein the composition has a pH between 6.0 to 7.0 and a viscosity of LV T-E @ 0.3 rpm of 150,000 cps.

2. The personal skin care composition of claim 1 further consisting essentially of about 0.08% to about 0.12%, based on the total weight of the composition, of sodium dehydroacetate.

3. The personal skin care composition of claim 1 further consisting essentially of about 2.4% to about 3.6%, based on the total weight of the composition, of isopentyldiol.

4. The personal skin care composition of claim 1 further consisting essentially of about 0.6% to about 0.9%, based on the total weight of the composition, of cetyl alcohol.

5. The personal skin care composition of claim 1 further consisting essentially of about 1.2% to about 1.8%, based on the total weight of the composition, of cetearyl alcohol and polysorbate 60.

6. The personal skin care composition of claim 1 further consisting essentially of about 0.6% to about 0.9%, based on the total weight of the composition, of tribehenin.

7. The personal skin care composition of claim 1 further consisting essentially of about 0.8% to about 1.2%, based on the total weight of the composition, of dimethicone.

8. The personal skin care composition of claim 1 further consisting essentially of about 0.8% to about 1.2%, based on the total weight of the composition, of biosaccharide Gum-1.

9. A personal skin care composition consisting of: (a) from about 50% to about 77%, based on the total weight of the composition, of water; (b) from about 0.6% to about 0.9%, based on the total weight of the composition, of a preservative mixture, said preservative mixture selected from the group consisting of phenoxyethanol, methylparaben, propylparaben, butylparaben, and isobutylparaben; (c) from about 8% to about 12%, based on the total weight of the composition, of a carbomer; (d) from about 4.2% to about 6.3%, based on the total weight of the composition, of tridecyl stearate; (e) from about 1.6% to about 2.4%, based on the total weight of the composition, of hydrogenated lecithin; (f) from about 1.2% to about 1.8%, based on the total weight of the composition, of behenyl alcohol; (g) from about 0.08% to about 0.12%, based on the total weight of the composition, of stearyl glycyrrhetinate; (h) from about 2.8% to about 4.2%, based on the total weight of the composition, of octyldodecyl myristate; (i) from about 0.1% to about 10%, based on the total weight of the composition, of squalane; (j) from about 0.16% to about 0.24%, based on the total weight of the composition, of an approximately 18% solution of sodium hydroxide and water; (k) from about 2.4% to about 3.6%, based on the total weight of the composition, of a mixture consisting of glucosamine HCl, red algae extract, yeast extract, and urea; (l) from about 0.24% to about 0.36%, based on the total weight of the composition, of benzalkonium chloride; (m) from about 0.16% to about 0.24%, based on the total weight of the composition, of tetrahexyldecyl ascorbate; (n) stoichiometrically balanced amounts of hydroxyl ions and stearates, wherein the hydroxyl ions are neutralized by the stearates; and (o) at least one of: (i) about 0.08% to about 0.12%, based on the total weight of the composition, of sodium dehydroacetate; (ii) about 2.4% to about 3.6%, based on the total weight of the composition, of isopentyldiol; (iii) about 0.6% to about 0.9%, based on the total weight of the composition, of cetyl alcohol; (iv) about 1.2% to about 1.8%, based on the total weight of the composition, of cetearyl alcohol and polysorbate 60; (v) about 0.6% to about 0.9%, based on the total weight of the composition, of tribehenin; (vi) about 0.8% to about 1.2%, based on the total weight of the composition, of dimethicone; or (vii) about 0.8% to about 1.2%, based on the total weight of the composition, of biosaccharide Gum-1.

* * * * *